United States Patent [19]
Annefors et al.

[11] Patent Number: 6,075,048
[45] Date of Patent: Jun. 13, 2000

[54] PEDIATRIC METHOD OF USE OF BAMBUTEROL

[75] Inventors: Staffan Annefors; Carl-Axel Bauer; Hans Nilsson, all of Lund, Sweden

[73] Assignee: Astra Aktiebolag, Sweden

[21] Appl. No.: 09/011,172

[22] PCT Filed: Dec. 9, 1997

[86] PCT No.: PCT/SE97/02053

§ 371 Date: Feb. 3, 1998

§ 102(e) Date: Feb. 3, 1998

[87] PCT Pub. No.: WO98/27981

PCT Pub. Date: Jul. 2, 1998

[30] Foreign Application Priority Data

Dec. 20, 1996 [SE] Sweden ................................. 9604752

[51] Int. Cl.⁷ .................................................. A61K 31/27
[52] U.S. Cl. .......................................................... 514/490
[58] Field of Search ............................................. 514/490

[56] References Cited

U.S. PATENT DOCUMENTS

| | | |
|---|---|---|
| 4,086,363 | 4/1978 | Cervoni et al. . |
| 4,419,364 | 12/1983 | Olsson et al. . |
| 4,451,663 | 5/1984 | Olsson et al. ............................. 560/29 |
| 4,499,108 | 2/1985 | Seiueira et al. . |

FOREIGN PATENT DOCUMENTS

| | | |
|---|---|---|
| 043 807 | 1/1982 | European Pat. Off. . |
| 9 200 629 | 11/1992 | Netherlands . |
| 2289842 | 12/1995 | United Kingdom . |
| WO 98/27981 | 7/1998 | WIPO . |

OTHER PUBLICATIONS

Berglund et al., "Screening chemical and physical stability of drug substances" Journal of Pharmaceutical & Biomedical Analysis 8:639–644 (1990).

Sitar et al., "A Placebo–controlled Dose–finding Study With Bambuterol in Elderly Patients With Asthma," Chest 3:771–776 (1993).

Clemmensen et al., "Bambuterol: clinical effects of three doses of bambuterol once daily in asthmatic patients," *Allergy*, 43:573–576 (1988).

McDonald, et al., "Comparison of Oral Bambuterol and Terbutaline in Elderly Patients with Chronic Reversible Airflow Obstruction," *Journal of Asthma*, 34:53–59 (1997).

*Primary Examiner*—Rebecca Cook
*Attorney, Agent, or Firm*—Fish & Richardson P.C.

[57] ABSTRACT

New aqueous formulations of, and the paediatric use of, bambuterol, and of its pharmaceutically acceptable salts, are described.

29 Claims, No Drawings

PEDIATRIC METHOD OF USE OF BAMBUTEROL

This is a continuation of International Patent Application No. PCT/SE97/02053, with an international filing date of Dec. 9, 1997, now pending.

This invention relates to a new pharmaceutical formulation and to its manufacture and use. It also relates to a new pediatric use of bambuterol.

Bambuterol, and its pharmaceutically acceptable salts, is known as a bronchodilator from EP 43807. Bambuterol is sold under the Trade Mark Bambec® in the form of tablets of its hydrochloride salt. Bambuterol is a pro-drug of the adrenergic selective $\beta_2$-receptor agonist terbutaline and is slowly metabolised in the body to active terbutaline.

There has been, and continues to be, an increase in the incidence of asthma amongst children. The administration of drugs to children, e.g. by way of inhalation or by means of tablets and capsules which are to be swallowed, can be difficult as the children, and especially younger children, do not always, or readily, co-operate. Furthermore some other patients find that a tablet is difficult to swallow, and if the tablet is chewed the drug in it can produce a bitter taste. Thus patient compliance when a tablet is prescribed is not always good.

We have now found that bambuterol can be formulated and administered in a more convenient form than a tablet.

Thus according to the invention we provide an aqueous formulation of bambuterol, or of a pharmaceutically acceptable salt thereof, wherein the formulation has a pH in the range 3.7 to 4.2.

We prefer the formulation to be adapted to be administered by swallowing.

We prefer the bambuterol to be in the form of its hydrochloride salt. The formulation is preferably a solution and preferably contains from about 0.5 to 5, e.g. about 1.0 mg, of bambuterol, measured as the hydrochloride, per ml.

The density of the formulation is preferably between about 1.03 and 1.09 g/ml.

We also prefer the pH of the formulation to be about 3.9. The pH of the formulation may be adjusted to the desired range or value by means of a suitable buffering agent, e.g. citric acid and if necessary sodium hydroxide. The skilled person will readily be able to find the appropriate quantity of buffering agent necessary to achieve the desired pH, but in general this will be in the range 3.0 to 5.0, e.g. about 4.0 mg/ml of citric acid, and from 0.4 to 0.8, e.g. about 0.6, mg/ml of sodium hydroxide.

The formulation may also contain a sweetening agent, e.g. sorbitol and/or glycerol, or a glucose polymer, for example that known as Lycasin®. The proportion of sweetening agent in the formulation will depend on the particular sweetening agent(s) used, but should be sufficient, together with any flavouring agent which is used, to cover the bitter taste of the bambuterol. We prefer the sweetening agent not to be such as to encourage dental caries. We prefer the formulation to contain from 100 to 200 mg, more preferably about 150 mg, per ml of sorbitol. We also prefer the formulation to contain from 75 to 125 mg, and more preferably about 100 mg, of glycerol per ml.

The formulation may also, e.g. when it is to be put up in a multi-dose form, contain a preservative, e.g. sodium benzoate. The preservative should be present in such a quantity as to produce a satisfactory preservative effect during its expected period of use. Thus we prefer the formulation to contain from 0.75 to 1.25 mg, and more preferably about 1.0 mg, per ml of sodium benzoate.

We have surprisingly found that the narrow pH range of the formulations according to the invention gives the optimal combination of stability of the active agent and of preservative action.

We have found that certain flavouring agents are incompatible with the desired formulation and/or with the containers to be used for the formulation. Suprisingly however we have found that no such incompatibilty exists when essence of blackcurrent is used. The essence of blackcurrent contains natural and synthetic flavours (which are identical to the natural flavours) in propylene glycol as solvent.

The unit and daily dosage of bambuterol to be used will depend on the patient and the type and severity of the condition to be treated.

One would expect that the dosage required for a child would be considerably lower than for an adult, i.e. a lower dosage proportionate to the child's, as compared to an adult's, body weight. Surprisingly we have found that this is not the case and that the dosage for children aged 6 and above, e.g. aged 6–12, is substantially the same as for an adult. The dosage for children aged below 6, e.g. from 2–5, is about one half of the adult dose. In both instances this is much more on a mg/kg basis than the corresponding adult dose.

We believe that the higher dose required for children is explained by an unexpected higher metabolic rate of the active ingredient in children as compared to adults.

Thus according to a further aspect of the invention we provide a method of treatment of a child in need of treatment with a bronchodilator, which comprises administering to the child a higher dose, as measured on an mg/kg basis, of bambuterol than the corresponding adult dose.

We prefer to administer a daily dose of from about 0.5 mg/kg to about 1.0 mg/kg of bambuterol, measured as the hydrochloride, to children aged from 2 to 5, and a dose of from about 0.14 mg/kg to about 1.0 mg/kg measured on the same basis to children aged from 6 to 12.

An adult unit dose of bambuterol comprises from 10 to 20 mg measured as the hydrochloride, i.e. 0.14 or 0.28 mg/kg for a 70 kg adult.

The dosage is generally given once a day for both children and adults.

According to the invention we also provide the use of bambuterol, or a pharmaceutically acceptable salt thereof, for the preparation of a paediatric medicament.

The paediatric medicament is preferably an aqueous formulation according to the invention, and may be put up as unit doses of the quantities given above or may be in the form of multiple doses, e.g. 100 or 300 ml units. The multiple doses may be packaged in any suitable container with which the formulation is compatible, e.g. a high density polyethylene bottle. The container is preferably fitted with a child resistant closure, which may also, or alternatively, be tamper evident.

The formulations according to the invention may be made by conventional pharmaceutical means, e.g. by simple mixing of the ingredients in the desired proportions.

The invention is illustrated, but in no way limited, by the following Examples

Example 1

Formulation in parts by weight

| | |
|---|---|
| Bambuterol hydrochloride | 1.0 |

-continued

Example 1

| | |
|---|---|
| Sorbitol 70% (non crystallising) | 150.0 |
| Glycerol | 100.0 |
| Sodium benzoate | 1.0 |
| Citric acid | 4.0 |
| Sodium hydroxide | 0.6 |
| Blackcurrent essence | 0.5 |
| Water purified to | 1,000 |

The formulation may be made by dissolving the sorbitol and glycerol in a portion of the water. The citric acid, sodium hydroxide, sodium benzoate and bambuterol hydrochloride are dissolved in a further portion of the water and the two solutions are then mixed. The blackcurrent essence is then added to the solution and the whole mixed, filtered and filled into containers. The pH of the solution is about 3.9.

EXAMPLE 2

Using the formulation of Example 1 several asthmatic children aged between 2 and 5 years were treated once daily, given in the evening, at a dose of 10 mg measured as bambuterol hydrochloride. The treatment was continued for up to 3 months. Effectiveness was evaluated from a daily diary (morning and evening) which included details re. asthma symptoms, use of rescue medication (inhaled beta-agonist), no. of awakenings due to asthma and PEF (peak expiratory flow). The treatment was effective.

What is claimed is:

1. A method of treatment of a child in need of treatment with a bronchodilator, which comprises administering to the child a higher dose, as measured on a mg/kg basis, of bambuterol, or of a pharmaceutically acceptable salt thereof, than the dose of bambuterol administered to an adult in need of the same treatment.

2. A method according to claim 1, wherein the child is aced 2 to 5 and the dose administered to the child is from 10 to 20 mg of bambuterol, measured as the hydrochloride salt, administered once a day.

3. A method according to claim 2, wherein the daily dose administered to the child is from 0.5 mg/kg to 1.0 mg/kg of bambuterol, measured as the hydrochloride salt.

4. A method according to claim 1, wherein the child is aged 2 to 5.

5. A method according to claim 1, wherein the daily dose administered to the child is from 0.5 mg/kg to 1.0 mg/kg of bambuterol, measured as the hydrochloride salt.

6. A method according to claim 1, wherein the bambuterol is administered as an aqueous formulation having a pH in the range 3.7 to 4.2.

7. A method according to claim 6, wherein the formulation is a solution containing 0.5 to 5 mg of banbuterol, measured as the hydrochloride salt, per ml.

8. A method according to claim 6, wherein the formulation comprises a buffering agent.

9. A method according to claim 6, wherein the formulation comprises a sweetening agent.

10. A method according to claim 6, wherein the comprises a blackcurrant flavoring.

11. A method according to claim 6, wherein the formulation has a density of 1.03 to 1.09 g/ml.

12. A method according to claim 2, wherein the bambuterol is administered as an aqueous formulation having a pH in the range 3.7 to 4.2.

13. A method according to claim 12, wherein the formulation is a solution containing 0.5 to 5 mg of bambuterol, measured as the hydrochloride salt, per ml.

14. A method according to claim 12, wherein the formulation comprises a buffering agent.

15. A method according to claim 12, wherein the formulation comprises a sweetening agent.

16. A method according to claim 12, wherein the formulation comprises a blackcurrant flavoring.

17. A method according to claim 12, wherein the formulation has a density of 1.03 to 1.09 g/ml.

18. A method according to claim 3, wherein the bambuterol is administered as an aqueous formulation having a pH in the range 3.7 to 4.2.

19. A method according to claim 18, wherein the formulation is a solution containing 0.5 to 5 mg of bambuterol, measured as the hydrochloride salt, per ml.

20. A method according to claim 18, wherein the formulation comprises a buffering agent.

21. A method according to claim 18, wherein the formulation comprises a sweetening agent.

22. A method according to claim 18, wherein the formulation comprises a blackcurrant flavoring.

23. A method according to claim 18, wherein the formulation has a density of 1.03 to 1.09 g/ml.

24. A method according to claim 4, wherein the bambuterol is administered as an aqueous formulation having a pH in the range 3.7 to 4.2.

25. A method according to claim 24, wherein the formulation is a solution containing 0.5 to 5 mg of banbuterol, measured as the hydrochloride salt, per ml.

26. A method according to claim 24, wherein the formulation comprises a buffering agent.

27. A method according to claim 24, wherein the formulation comprises a sweetening agent.

28. A method according to claim 24, wherein the formulation comprises a blackcurrant flavoring.

29. A method according to claim 24, wherein the formulation has a density of 1.03 to 1.09 g/ml.

* * * * *